(12) United States Patent (10) Patent No.: US 8,206,279 B2
Ugander et al. (45) Date of Patent: Jun. 26, 2012

(54) SURGICAL METHOD

(75) Inventors: Martin Ugander, Malmö (SE); Malin Malmsjö, Lund (SE)

(73) Assignee: Shieldheart MedTech AB, Lund (SE)

( * ) Notice: Subject to any disclaimer, the term of this patent is extended or adjusted under 35 U.S.C. 154(b) by 1294 days.

(21) Appl. No.: 11/746,712

(22) Filed: May 10, 2007

(65) Prior Publication Data

US 2008/0058684 A1 Mar. 6, 2008

(30) Foreign Application Priority Data

Sep. 4, 2006 (SE) ...................................... 0601825

(51) Int. Cl.
*A61F 13/00* (2006.01)
(52) U.S. Cl. .......................................................... 600/37
(58) Field of Classification Search .................. 128/897, 128/898; 601/6, 7; 602/42
See application file for complete search history.

(56) References Cited

U.S. PATENT DOCUMENTS

| | | | |
|---|---|---|---|
| 5,437,651 A * | 8/1995 | Todd et al. ..................... | 604/313 |
| 5,645,081 A * | 7/1997 | Argenta et al. ............... | 128/897 |
| 6,695,823 B1 * | 2/2004 | Lina et al. ..................... | 604/304 |
| 6,752,794 B2 * | 6/2004 | Lockwood et al. ............ | 604/313 |
| 7,361,184 B2 * | 4/2008 | Joshi ............................. | 606/213 |
| 7,504,549 B2 * | 3/2009 | Castellani et al. ............. | 602/41 |
| 2001/0029956 A1 | 10/2001 | Argenta et al. | |
| 2004/0073151 A1 * | 4/2004 | Weston .......................... | 602/41 |
| 2005/0186260 A1 * | 8/2005 | Narini et al. .................. | 424/445 |

FOREIGN PATENT DOCUMENTS

WO 0064394 11/2000
WO 2004041346 5/2004

* cited by examiner

*Primary Examiner* — Samuel Gilbert
(74) *Attorney, Agent, or Firm* — Gesmer Updegrove LLP

(57) ABSTRACT

The present invention relates to a method at surgical operations applying negative pressure wound treatment as a post-surgical event, whereby the pressure around an organ or tissue is distributed by applying an open cell structure around the organ or tissue avoiding a move of the organ or tissue as such.

17 Claims, 2 Drawing Sheets

SURGICAL METHOD

PRIORITY

The present application claims priority to Swedish Application No. 0601825-3, filed on Sep. 4, 2006 which is incorporated herein by reference in its entirety.

DESCRIPTION

1. Technical Field

The present invention relates to a new surgical method, in particular a new method in relation to negative pressure wound treatment.

2. Background of the Invention

In 1997, Morykwas and Argenta published three landmark articles regarding experience with a "new method for wound control and treatment." A system was described where subatmospheric pressure was applied through a closed system to an open wound for periods of 48 hours. Subatmospheric pressure was directed at the surface of the wound through an interface between the wound surface and a polyurethane sponge to allow for distribution of the negative pressure using either a constant or intermittent mode based on clinical experience.

Negative pressure wound therapy is thought to promote wound healing through multiple actions—e.g., removing exudate from wounds to help establish fluid balance, providing a moist wound environment, and removing slough; and potentially decreasing wound bacterial burden, reducing edema and third-space fluids, increasing blood flow to the wound, increasing growth factors, and promoting white cells and fibroblasts within the wound.6

The definition of Negative Pressure Wound Therapy varies but independent definitions centre around negative pressure in the wound bed: Thus it has been defined as "Negative Pressure Therapy is the application of subatmospheric pressure either continuously or intermittently to an open wound" or "Negative Pressure Wound Therapy is a non-invasive treatment by which controlled localized negative pressure is delivered to a wide variety of acute, sub-acute and chronic wounds"

Negative pressure wound therapy (NPWT, or TNP treatment as it will be called in the following) is a topical treatment intended to promote healing in acute and chronic wounds. It involves the application of negative pressure (suction) to the wound bed.

TNP involves application of a non-adherent, porous wound dressing, a drainage tube placed adjacent to or inserted in the dressing, an occlusive transparent film sealing the wound and the drainage tube, and a connection to a vacuum source, which supplies the negative pressure. The concept is to turn an open wound into a controlled, closed wound while removing excess fluid from the wound bed, thus enhancing circulation and disposal of cellular waste from the lymphatic system.

This technique is usually considered for chronic wounds (those that fail to progress through the normal phases of healing—inflammation, proliferation, maturation—and thus do not heal), acute wounds (wounds that are expected to heal and demonstrate evidence of progression through the phases of healing), and difficult wounds (wounds with such associated factors as diabetes, arterial insufficiency, and venous insufficiency). Common applications for NPWT appear in following Table.

Acute wounds
Partial- and full-thickness burns
Surgically created wounds and surgical dehiscence*
Neuropathic (diabetic) wounds
Venous or arterial insufficiency ulcer unresponsive to standard therapy
Traumatic wounds (i.e., flap or meshed graft)
Pressure ulcers (stage 3 or 4)
*Patients with other medical problems; i.e., diabetes, coronary artery disease, or renal disease, may be more susceptible to wound dehiscence and delayed wound healing. NPWT seems to provide increased wound stability.

In cardiac surgery, e.g., by-pass operation of the heart, the sternum is cut lengthwise, and quite often the left pleura is opened as well. This generates a so called sternotomy wound. Following surgery, the sternotomy wound is closed with sternal wires and left to heal. In a number of patients, about 1 to 5% of those undergoing cardiac surgery including sternotomy, an infection called mediastinitis occurs. Such poststernotomy mediastinitis occurs in particular in a risk group of patients, such as those suffering from diabetes mellitus, low left ventricular ejection fraction, obesity, renal failure, and three-vessel disease.

Established treatment of poststernotomy mediastinitis includes debridement with frequent postoperative irrigation, change of wound dressings and direct secondary closure or secondary closure by use of vascularized muscle flaps. The reported early mortality using these established techniques in poststernotomy mediastinitis following coronary bypass surgery is between 8 and 25%. However, the introduction of a technique for using topical negative pressure (TNP) to treat poststernotomy mediastinitis has essentially reduced the mortality due to mediastinitis to 0% (Sjogren, J., et al. Ann Thorac Surg. 80: 1270, 2005). The TNP technique entails applying negative pressure to a wound in a controlled manner. A wound dressing in the form of a sterile polyurethane foam is placed between the sternal edges, but not below the level of the sternum, in order not to affect hemodynamic and respiratory function. A second layer of foam is often placed subcutaneously and secured with a running suture to the surrounding skin. This facilitates the application of the adhesive drape and reduces the risk of accidental movement of the device. Drainage tubes are inserted into the foam. The wound is then sealed with a transparent adhesive drape. The drainage tubes are connected to a purpose-built vacuum pump and a canister for collection of effluents. Initially, a low pressure (e.g. −50 mmHg) is applied to allow adjustment of the foam as the air is evacuated. If the wound geometry and foam contraction are considered satisfactory, a higher subpressure of e.g. −125 mmHg is applied. Air leakage is known to dry out the wound and can be prevented by additional draping. Most of the patients can be extubated and mobilized immediately after TNP application. Revisions and dressing changes are performed regularly, e.g. three times a week, under aseptic conditions and general anesthesia. The sternal wound can be closed and rewired when the infection has resolved, typically after 1-3 weeks of TNP treatment. The method is simple and effective and is believed to combine the benefits of closed and open wound treatment to create an environment that promotes wound healing.

However, a very serious potential complication of TNP therapy of sternotomy wounds is the risk for serious damage to the heart and surrounding structures, in particular rupture of the right ventricle of the heart. Two cases of right ventricular rupture have been described in the literature (Abu-Omar, Y., et al. Ann Thorac Surg. 76: 974; author reply 974, 2003). A total of 36 cases of heart rupture have been reported as of February 2006 (unpublished data). Also, the method is known to impair the hemodynamic function (Conquest, A. M., Garofalo, J. H., Maziarz, D. M., et al. Hemodynamic effects of the vacuum-assisted closure device on open mediastinal wounds. *J Surg Res.* 115: 209, 2003).

It is established that post sternotomy mediastinitis can be effectively treated using TNP, but it is a major concern that the method is not completely reliable and can cause heart rupture and impairment of heart function.

Thus heart rupture is a devastating complication of VAC or TNP therapy of mediastinitis following cardiac surgery. However, little is known about the macroscopic effects of VAC therapy on the intrathoracic anatomy. Therefore one aim has been to examine the effect of negative pressure application on the heart using MRI in a porcine sternotomy wound model.

SUMMARY OF THE PRESENT INVENTION

The cause of heart rupture or right ventricle rupture of the heart is due to the fact that heart is sucked into the space between the sternum halves and will become clamped by these halves due to the subpressure applied. The inventors of the present application have previously proposed a barrier disk to be introduced to prevent the heart from be clamped by the sternum halves. However the primary cause of this movement of the heart has not been previously contemplated, neither has a primary solution to the problem been identified.

DETAILED DESCRIPTION OF THE PRESENT INVENTION

The present invention relates to a new method for surgical treatment using topical negative pressure (TNP), and in particular the invention is characterized in that (i) an organ or tissue is enclosed in a foam material having an open cell structure (ii) that a the negative pressure is applied via NPWT on all sides of the said cell structure eliminating body liquid via said cell structure and simultaneously keeping the organ substantially in place.

In a primary aspect of the invention it relates to a method at surgical operations applying negative pressure wound treatment as a post-surgical event, whereby the pressure around an organ or tissue is distributed by applying an open cell structure around the organ or tissue avoiding displacement of the organ or tissue as such.

In accordance with a preferred embodiment the pressure is distributed using a foamed polymer having an open cell structure enwrapping the organ or tissue in question.

In accordance with a further preferred embodiment the negative pressure used at the negative pressure wound treatment is at least 15 mmHg, preferably at least 25 mmHg, more preferably 40 mmHg, still more preferably 75 mmHg.

In accordance with a further preferred embodiment pressure is transmitted to all parts of the wound via an open pore structure material or sheet that is placed in the spatium between organs and tissues of the wound.

In accordance with a further preferred embodiment the pressure is distributed after thorax surgery.

In accordance with a further preferred embodiment the pressure is distributed after abdominal surgery.

In accordance with a further preferred embodiment the pressure is distributed after brain surgery.

In accordance with a further preferred embodiment the pressure is distributed after neuropathic surgery.

In accordance with a further preferred embodiment the pressure is distributed at the treatment of pressure ulcers.

In accordance with a further preferred embodiment the pressure is distributed at the treatment of partial- and full-thickness burns.

In accordance with a further preferred embodiment the pressure is distributed at the treatment of surgical dehiscence.

In accordance with a further preferred embodiment the pressure is distributed at the treatment of traumatic wounds.

In accordance with a further preferred embodiment the pressure is distributed at the treatment of venous or arterial insufficiency ulcer unresponsive to standard therapy

BRIEF DESCRIPTION OF THE DRAWINGS

The present invention will be described in detail in the following with reference to the accompanying drawings prepared from MRIs obtained, wherein.

Figure 1A:
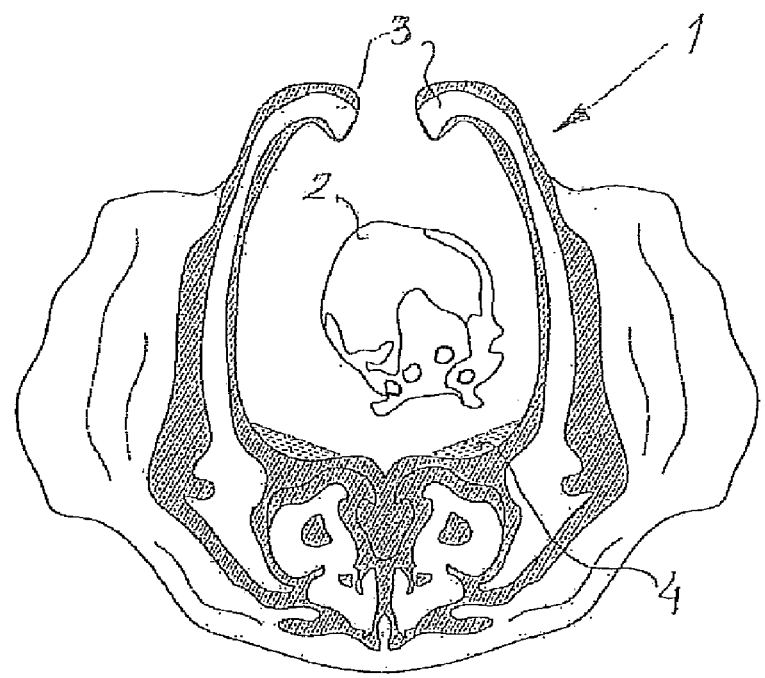
FIG. 1A shows a first image in a transverse plane of an sternotomised pig, the TNP equipment has been applied including the subpressure at time point 0.
Figure 1B:
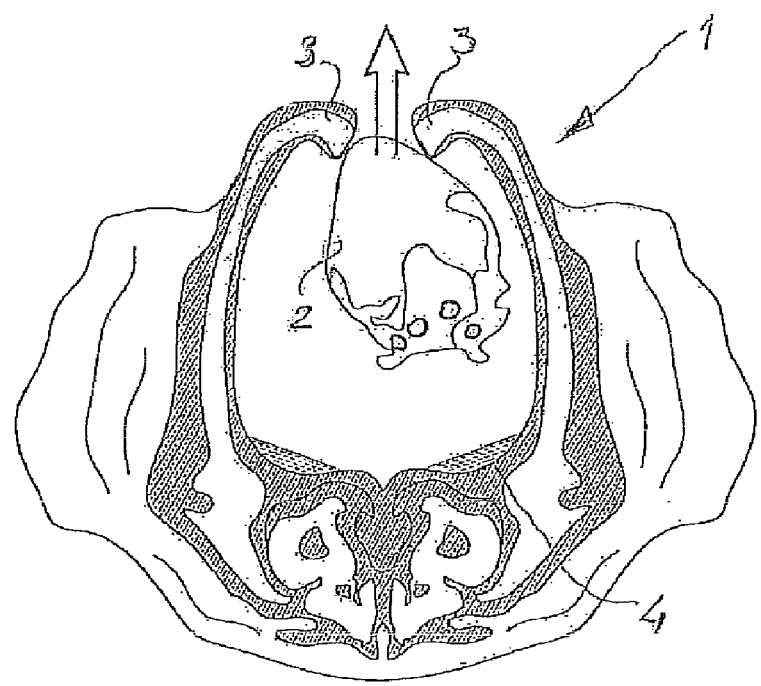
FIG. 1B shows a second image one hour later in relation to the image of FIG. 1A after application of a subpressure of −50 mmHg.

In the figures 1 generally denotes a thorax region with a heart 2. The sternum 3 has been opened surgically. To close the sternum using TNP a subpressure equipment is applied (not shown), but indicated with an open arrow in FIGS. 1B and 2B. Body liquid gathered is denoted 4.

In FIG. 1A no subpressure has been applied to the thorax, and as evident the heart is normally centered in the thorax. After having applied a subpressure of −50 mmHg the heart 2 has moved upwards (FIG. 1B) and is present in the risk zone of being clamped by the opened sternum edges 3.

Figure 2A:
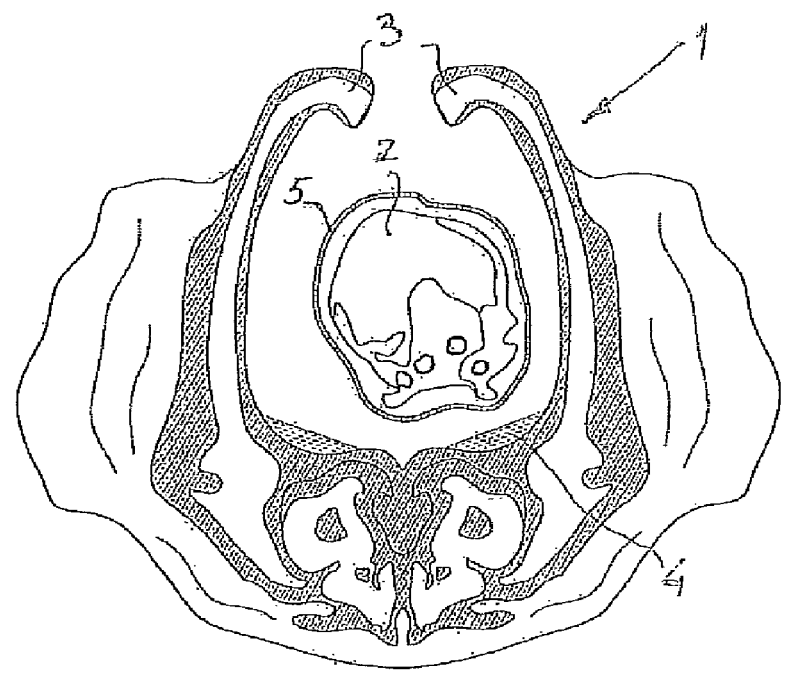
FIG. 2A shows an image of a thorax-sternotomised pig, where an open pore structure wrapping has been applied around the heart at time point 0.

In FIG. 2A the heart 2 has been wrapped into an open pore structure material 5, which facilitates distribution of the pressure in the thorax during TNP, as well as it facilitates transport of body fluid gathered in the bottom, back region of the thorax. Such removal of the liquid supports healing and reduces the risk for any further infections in the thorax.

As evident from the attached images a heart during TNP tends to move towards the surface where TNP is being applied and to become clamped by the sternal edges. It has become apparent that this movement of the heart is due to a difference in pressure on either sides of the heart. In this case the heart with surrounding tissue will close against the sternum area whereby the subpressure applied over the sternum region during TNP will differ from the pressure present in the thorax cavity causing the heart to move towards the sternum.

To eliminate this problem the pressure is to be distributed around the heart, whereby the heart will not move out of place but will remain at its normal site, and thereby, besides eliminating the mechanical clamping by the sternum edges, will reduce rupture inducing forces applied to the heart at such treatments.

One way of distributing the pressure around the heart is to apply a foamed polymer having an open cell structure allowing air and liquid to pass from one end thereof to the other, e.g., by gravitation or by reduced pressure. When applying a subpressure to the TNP equipment, i.e., air tight sheets, dressings, and foams, the same pressure will be applied elsewhere in the thorax region preventing the heart from being forced towards the subpressure side. Furthermore, surprisingly, the body liquid collected in the thorax region, primarily at the back region of the thorax region will be sucked up by the foamy cell structure and will become transported to the TNP equipment. However, the heart will not move to any substantial degree towards to sternum edges. Thus any body liquid or exudates formed will be drained from the lower cavities as well. The TNP equipment as such will drain the wound area, such as the wound area between a divided sternum as well as the said body liquid or exudates.

Thus, distribution of the pressure around organs and between tissues can be obtained by placing an open pore structure material (or sheet) in the spatium between the organs thereby allowing pressure transduction to the bottom of the wound and around the tissue or organ in question.

Six pigs underwent median sternotomy. Real time MRI (magnet x-ray imaging) (10 images/s) was performed in a midventricular transverse and a midsagittal plane during the application of negative pressure. Imaging was performed after the insertion of two different devices. (1) A roughly 10×20×0.2 cm perforated plastic rigid barrier placed inside the thorax between the heart and the sternal edges. (2) An open porous structure material (1 cm thick) was placed underneath the heart with preserved communication to the intersternal foam to facilitate pressure transduction to the bottom of the wound.

Two potentially hazardous events were observed during the application of negative pressure. (1) The anterior portion of the right ventricular free wall was sucked up towards the anterior thoracic wall and bulged into the space between the sternal edges, and (2) the sharp edges of the sternum jutted into and deformed the anterior surface of the heart. These events were prevented by the application of either of the two devices described above.

Inserting a rigid barrier prevents the heart from being sucked up into or deformed by the sternal edges. Pressure transduction to the bottom of the wound seems to hinder the heart from being sucked up into the intersternal space and against the sharp sternal edges. These two approaches may prevent heart rupture.

Prior to the application of negative pressure, the heart is located centrally in the thorax and clearly separated by air from the anterior thoracic wall (FIGS. 1 and 2). When negative pressure is applied, the following events could be clearly observed in all pigs. The air separating the heart from the thoracic wall is evacuated whereby the heart is sucked up towards the anterior thoracic wall. Simultaneously, the diastasis between the sternal edges decreases and the polyurethane foam is compressed. The transverse and two chamber imaging planes together illustrate the immediate proximity between the entire heart, encompassing the left and right ventricles from the base to the apex, and the anterior thoracic wall following the application of negative pressure.

No apparent differences in heart displacement when taking no precautions to avoid movement of the heart could be observed with regards to the effect of different magnitudes of negative pressure (75, 125 or 175 mmHg).

In two pigs, it was observed in the transverse plane that the anterior portion of the right ventricular free wall was sucked up and bulged into the diastasis between the sternal edges, thereby mimicking an aneurysm. In one different pig, the two hemisternum edges did not oppose at the same level due to left-sided cracked ribs at the time of harvesting the left internal mammary artery. This resulted in a sharp and uneven edge of the split sternum protruding into the thoracic cavity. Upon application of negative pressure, the transverse imaging plane revealed how the heart was sucked up toward the anterior thoracic wall, and the left hemisternum jutted into and deformed the anterior surface of the heart.

The effect of different interface dressing on the protection of the heart was evaluated. A paraffin gauze dressing slightly separated the heart from the anterior thoracic wall while retaining the contours of the thoracic wall. After inserting a rigid barrier, the heart still approached the anterior thoracic wall but the shape of the heart was not affected.

As evident from FIG. 1A the heart is present in its normal position at time point 0, while after application of −125 mmHg, the heart has moved upwards to come into close contact with the sternum, FIG. 1B.

Figure 2B:
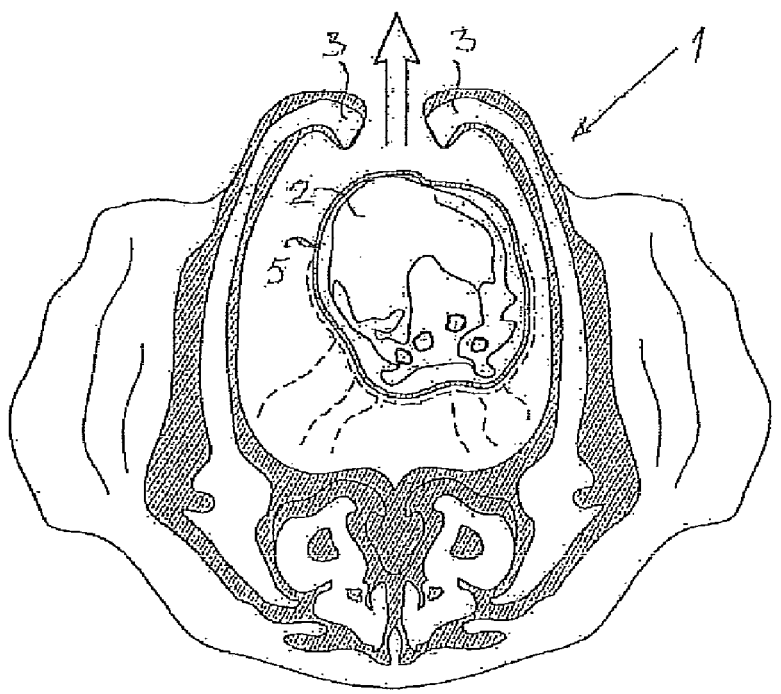
FIG. 2B shows an image of the pig one hour later in relation to FIG. 2A after application of a subpressure of −50 mmHg.

FIGS. 2A to 2B show an image where the present invention has been applied, and from which it is evident that the heart does not rise to come in close contact with the sternum after application of a subpressure of −125 mmHg has been applied. It is thus evident that the present methodology solves the problem presented.

In the present method the negative pressure used at the negative pressure wound treatment is at least 15 mmHg, preferably at least 25 mmHg, more preferably 40 mmHg, still more preferably 75 mmHg and may reach 125 to 175 mmHg or even higher.

The invention claimed is:

1. A method at surgical operations applying negative pressure wound treatment as a post-surgical event, whereby the negative pressure around an organ or tissue is distributed by applying an open pore structure material or sheet around the organ or tissue avoiding movement of the organ or tissue as such to any substantial degree wherein the pressure is distributed using the open pore structure material or sheet enwrapping the organ or tissue in question.

2. A method according to claim 1, wherein the negative pressure used at the negative pressure wound treatment is at least 15 mmHg.

3. A method according to claim 1, wherein the pressure is distributed after thorax surgery.

4. A method according to claim 1, wherein the pressure is distributed after abdominal surgery.

5. A method according to claim 1, wherein the pressure is distributed after brain surgery.

6. Method according to claim 1, wherein the pressure is distributed after neuropathic surgery.

7. A method according to claim 1, wherein the pressure is distributed at the treatment of pressure ulcers.

8. A method according to claim 1, wherein the pressure is distributed at the treatment of partial- and full-thickness burns.

9. A method according to claim 1, wherein the pressure is distributed at the treatment of surgical dehiscence.

10. A method according to claim 1, wherein the pressure is distributed at the treatment of traumatic wounds.

11. A method according to claim 1, wherein the pressure is distributed at the treatment of venous or arterial insufficiency ulcer unresponsive to standard therapy.

12. A method according to claim 1, facilitating elimination of body fluid from a wound.

13. A method according to claim 1, wherein the negative pressure used at the negative pressure wound treatment is at least 15 mmHg at least 25 mmHg.

14. A method according to claim 1, wherein the negative pressure used at the negative pressure wound treatment is at least 15 mmHg at least 40 mmHg.

15. A method according to claim 1, wherein the negative pressure used at the negative pressure wound treatment is at least 15 mmHg at least 75 mmHg.

16. A method according to claim 1, wherein said open pore structure material or sheet is a foam material.

17. A method according to claim 1, wherein said open pore structure material or sheet is a foamed polymer.

* * * * *